United States Patent
Kadziauskas et al.

(10) Patent No.: US 7,373,850 B2
(45) Date of Patent: May 20, 2008

(54) TEST CHAMBER FOR BI-MANUAL LENS EXTRACTION

(75) Inventors: Kenneth E. Kadziauskas, Coto de Caza, CA (US); Mark E. Steen, Chino Hills, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 561 days.

(21) Appl. No.: 10/290,700

(22) Filed: Nov. 8, 2002

(65) Prior Publication Data
US 2004/0089080 A1   May 13, 2004

(51) Int. Cl.
*G01N 33/00* (2006.01)
(52) U.S. Cl. ...................................... 73/865.9
(58) Field of Classification Search ............... 73/865.8, 73/865.9, 863.71, 863.72, 863.73; 604/22, 604/35, 43–45, 27, 119; 606/107, 169; 134/43
See application file for complete search history.

(56) References Cited

U.S. PATENT DOCUMENTS

| | | | |
|---|---|---|---|
| 4,386,927 A | 6/1983 | Eichenbaum | |
| 4,493,694 A | 1/1985 | Wuchinich | |
| 4,531,934 A | 7/1985 | Kossovsky et al. | |
| 4,689,040 A | 8/1987 | Thompson | |
| 4,959,049 A | 9/1990 | Smirmaul | |
| 5,213,569 A | 5/1993 | Davis | |
| 5,257,988 A | 11/1993 | L'esperance, Jr. | |
| 5,299,591 A * | 4/1994 | Duncan ................... | 73/863.71 |
| 5,413,556 A | 5/1995 | Whittingham | |
| 5,429,601 A * | 7/1995 | Conley et al. ................ | 604/65 |
| 5,653,724 A | 8/1997 | Imonti | |
| 5,695,461 A | 12/1997 | Schaible | |
| 5,718,676 A | 2/1998 | Barrett | |
| 5,725,495 A | 3/1998 | Strukel et al. | |
| 5,741,226 A | 4/1998 | Strukel et al. | |
| 5,741,244 A | 4/1998 | Klaas | |
| 5,743,871 A | 4/1998 | Strukel et al. | |
| 5,746,713 A | 5/1998 | Hood et al. | |
| 5,788,679 A | 8/1998 | Gravlee, Jr. | |
| D399,557 S | 10/1998 | Hood et al. | |
| 5,830,192 A | 11/1998 | Van Voorhis | |
| 5,935,096 A | 8/1999 | Barrett | |
| 5,989,209 A | 11/1999 | Barrett | |
| 5,993,408 A | 11/1999 | Zaleski | |
| 5,993,409 A * | 11/1999 | Maaskamp ................... | 604/22 |
| 6,007,555 A | 12/1999 | Devine | |

(Continued)

FOREIGN PATENT DOCUMENTS

DE    41 31 401 C1    9/1991

(Continued)

OTHER PUBLICATIONS

Definition of "irrigate" from The American Heritage Dictionary, 1982.*

*Primary Examiner*—Robert Raevis

(57) ABSTRACT

Test apparatus for bi-manual phaco needle apparatus are provided which includes a chamber for establishing a fluidic circuit between an irrigation needle and an aspiration needle. A first inlet into the chamber is provided for establishing a sealed communication with the irrigation needle and a second inlet is provided for establishing a sealed fluid communication with an aspiration needle. The apparatus enables a method for testing bi-manual phacoemulsification apparatus and priming thereof.

8 Claims, 1 Drawing Sheet

U.S. PATENT DOCUMENTS

| | | |
|---|---|---|
| 6,013,046 A | 1/2000 | Maaskamp et al. |
| 6,013,049 A * | 1/2000 | Rockley et al. ............... 604/22 |
| 6,083,192 A * | 7/2000 | Bath ........................... 604/22 |
| 6,126,629 A | 10/2000 | Perkins |
| 6,135,991 A | 10/2000 | Muni et al. |
| 6,299,591 B1 | 10/2001 | Banko |
| 6,432,078 B1 * | 8/2002 | Peyman ...................... 604/27 |
| 6,506,176 B1 * | 1/2003 | Mittelstein et al. ........... 604/22 |
| 2002/0134716 A1 | 9/2002 | Maartens et al. |
| 2004/0089330 A1 * | 5/2004 | Muller ................... 134/167 R |

FOREIGN PATENT DOCUMENTS

| | | |
|---|---|---|
| JP | 2000-237228 A | 9/2000 |

* cited by examiner

TEST CHAMBER FOR BI-MANUAL LENS EXTRACTION

The present invention generally relates to phacoemulsification apparatus and is more particularly directed to test apparatus for bi-manual phaco needle apparatus.

By way of background, phacoemulsification apparatus is utilized for surgically removing cataractic lenses and replacing same with an artificial interocular lens.

Cataract removal was first effected through manual surgical procedures which necessitated the cutting of the cornea resulting in a wound of up to 12 mm in length.

Since these large wounds can result in corneal or scleral tissue damage, phacoemulsification procedures have been developed in which a needle is inserted through an incision into a lens capsule and needle is ultrasonically vibrated to mechanically emulsify the lens. The incision required for this procedure has been typically about 2.5 to about 4 mm. Once fragmented, or emulsified, the lens material is then aspirated from the lens capsule.

Phacoemulsification apparatus may include a handpiece having a coaxial assembly which includes a needle with an aspiration lumen therethrough and a sleeve disposed over the needle for establishing an annulus for providing irrigation fluid over the needle. While the sleeve surrounding a phacoemulsification needle provides an important function of establishing the annulus for introducing irrigation fluid into the lens capsule it unfortunately necessitates a larger overall diameter for which an incision must be made.

Other phacoemulsification apparatus known as, "bi-manual" phacoemulsification apparatus utilizes two needles, one for introducing an irrigation fluid into a lens capsule and another ultrasonically vibrated needle for inserting into the lens capsule for emulsifying the lens tissue therein. Such apparatus is described in U.S. patent application Ser. No. 09/894,503 "Bi-Manual Phaco Needle" filed on Jun. 28, 2001. This application is to be incorporated herein in its entirety, including all drawings and specifications for the purpose of describing apparatus for which the present invention is useful for testing.

SUMMARY OF THE INVENTION

Test apparatus in accordance with the present invention for bi-manual phaco needle apparatus generally includes a chamber for establishing a fluidic circuit, a first inlet into the chamber for establishing fluid communication with an irrigation needle and a second inlet into the chamber for establishing fluid communication with an aspiration needle.

In one embodiment of the present invention, the first and second inlets are disposed proximate one another on one end of the chamber and in another embodiment of the present invention, the first and second inlets are disposed on opposite ends of the chamber.

The chamber thus provides a fluidic circuit to assist in priming fluids in irrigation and aspiration lines as well as assist in the process of air bubble elimination from the irrigation line.

More particularly, the first inlet may be sized for sealing around the irrigation needle and the second inlet is sized for sealing around a handpiece supporting the aspiration needle. In this manner, the bi-manual phacoemulsification apparatus requires no further adjustment or modification upon completion of a testing and is thereafter immediately ready for use in a subsequent phacoemulsification procedure.

Preferably, the chamber is formed from a transparent material for enabling visual monitoring of the fluidic circuit. As noted above, this assists in the process of air bubble elimination from the irrigation line.

A method in accordance with the present invention for testing bi-manual phacoemulsification apparatus generally includes the steps of providing a sealed chamber having a first inlet for an irrigation needle and a second inlet for an aspiration needle, thus establishing a fluidic circuit therebetween.

Irrigation fluid is introduced into the chamber with the irrigation needle and such introduced fluid is aspirated through an aspiration needle.

Preferably, the chamber is sealed and the method includes the use of a transparent chamber in order that the step of visually monitoring the fluidic circuit through chamber walls is enabled.

The method in accordance with the present invention may further include the step of circulating irrigation fluid through the chamber for the elimination of air bubbles in the fluid, which may be observed following the filling of the chamber with irrigation fluid.

The method may include, alternatively, the step of providing a chamber having the first and second inlets proximate one into the chamber or in which the chamber is provided with first and second inlets disposed on opposite ends of the chamber.

More particularly, method, in accordance with the present invention, may provide for priming bi-manual phacoemulsification apparatus which includes the steps of introducing irrigation fluid into a sealed chamber with an irrigation needle and aspirating the introduced fluid with an aspiration needle. As noted hereinabove, the sealed chamber establishes a fluidic circuit between the irrigation needle and the aspiration needle.

BRIEF DESCRIPTION OF THE DRAWINGS

The advantages and features of the present invention will be better understood by the following description when considered in conjunction with the accompanying drawings in which.

DETAILED DESCRIPTION

Figure 1:
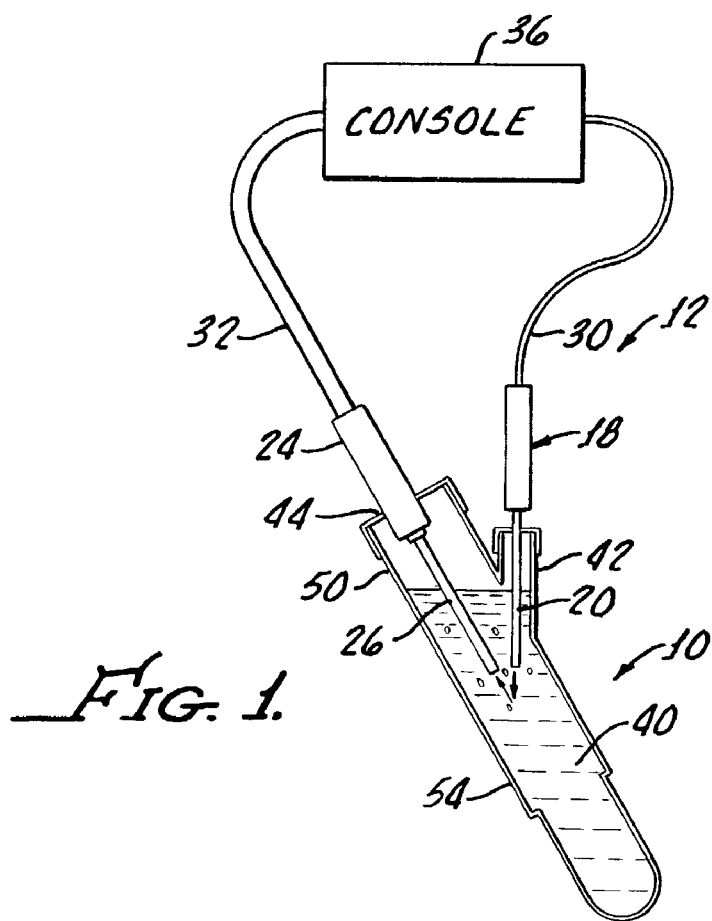
FIG. 1 is a diagram of test apparatus in accordance with the present invention as it may be used with bi-manual phacoemulsification apparatus generally showing a chamber for establishing a fluidic circuit between an irrigation needle and an aspiration needle with the apparatus including first and second inlets disposed proximate one end of the chamber.

With reference to FIG. 1, there is shown test apparatus 10 in accordance with the present invention for bi-manual phaco apparatus 12 which generally includes an irrigation handpiece 18 having an irrigation needle 20 and aspiration handpiece 24 including an aspiration needle 26. Both the irrigation handpiece 18 and aspiration handpiece 24 communicate through lines 30, 32 to a console 36. Operation of the handpieces 18, 24 and console 36 is described in U.S. Ser. No. 09/894,503 hereinabove referenced and incorporated herein. Accordingly, no further description of the use of the bi-manual phaco apparatus 12 for removal of cataractic tissue is discussed herein.

However, the use of separate irrigation needles 20 and aspiration needles 26 necessitates priming of fluids, particularly through lines 30, 32 and the elimination of air bubbles and otherwise confirming proper operation of the phacoemulsification apparatus 12.

The test apparatus 10 preferably includes a chamber 40 which is formed from a transparent silicone which enables visual monitoring of the fluidic circuit established therein by the irrigation needle 20 and aspiration needle 26. However, other suitable materials may be utilized in the formation of the chamber 40 which can be produced in any conventional manner. A flexible chamber 40 has the advantage of assisting a user in identifying fluidic balance within the apparatus 12 by simulation of flexibility of a lens capsule (not shown). That is, the size and wall thickness may be determined to provide comparable lens capsule dynamics.

A first inlet 42 formed in the chamber 40 is provided for establishing fluid communication with the irrigation line 30, preferably with the irrigation handpiece 18 or irrigation needle 20. While the first inlet 42 is illustrated in an engaging relationship with the needle 20, it may be sized for engaging the handpiece 18 or with direct engagement with the line 30 through a fitting, not shown. A second inlet 44 formed in the chamber 40 is provided for establishing fluid communication with the aspiration line 32, preferably with the aspiration handpiece 24, as shown or directly with the aspiration needle 26. Again fluid communication may be established directly with the aspiration line 32 through a fitting, not shown. The second inlet 44 may be sized for sealing around the handpiece 24 supporting the needle 26 and the first inlet 42 may be sized for sealing around the irrigation needle 20. Alternatively, inlets (not shown) may be formed in the chamber 40 receiving only the needles 20, 26 or one or both of the handpieces 18, 24.

The advantage of sealing around the handpiece is 18, 26 rather than the needles 20, 26 is to facilitate handling of the needles and test apparatus 10. That is, to reduce direct handling of the needles 20, 26 which, of course, may inadvertently cause injury to a user if not properly manipulated.

In the embodiment 10, the first and second inlets 42, 44 are formed proximate one end 50 of the chamber 40.

Figure 2:
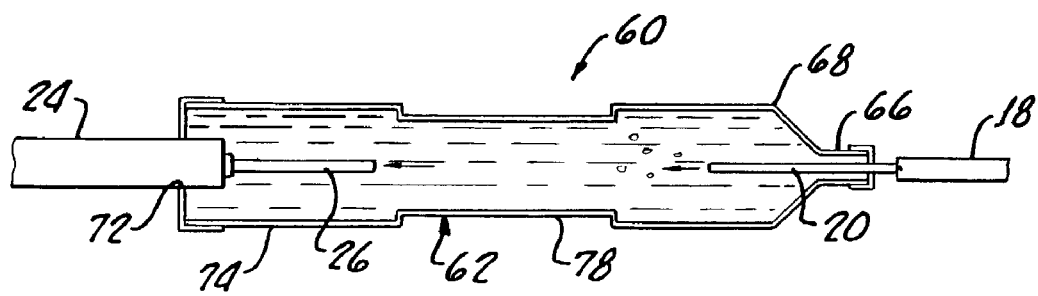
FIG. 2 is a diagram of apparatus similar to that shown in FIG. 1 showing a chamber for establishing a fluidic circuit between an irrigation needle and an aspiration needle with the use of first and second inlets disposed on opposite ends of the chamber.

With reference to FIG. 2, there is shown another embodiment 60 in accordance with the present invention utilizing a chamber 62 for establishing a fluidic circuit between the irrigation needle 20 and the aspiration needle 26. Common reference numbers illustrated in FIG. 2 correspond to identical or similar structure as shown in FIG. 1.

The chamber 62 includes a first inlet 66 disposed in a first end 68 of the chamber 62 for sealably receiving the irrigation needle 20 and a second inlet 72 disposed on an opposite end 74 of the test chamber 62 for receiving the handpiece 24 and establishing fluid communication with the aspiration needle 26.

The chamber 62 may include a necked down portion 78 for enhancing visual acuity of any bubbles in irrigation fluid in the chamber 62 after filling with the irrigation needle 20.

The test apparatus 10, 60 hereinabove describe enables a method of the present invention for testing bi-manual phacoemulsification apparatus including priming thereof. Priming involves the filling of lines 30, 32 (see FIG. 1) through appropriate pumping and vacuum action provided by the console 36. Typically, the fluid comprises a saline solution and it is important to remove any gaseous formation, such as bubbles, not shown, from the apparatus 12 before a phacoemulsification procedure is performed.

Accordingly, a method in accordance with the present invention includes the steps of providing a sealed chamber at 40 with the first inlet 42 for the irrigation needle 20 and the second inlet 44 for the aspiration needle 26.

In the method, irrigation fluid is introduced into the chamber preferably filling the same and aspirating the introduced fluid with the aspiration needle 26.

Providing of a sealed transparent chamber 40 enables the step of visually monitoring the fluidic circuit through the chamber walls 54 or necked down portion 78 in chamber 60 (see FIG. 2).

The method further includes a step of providing the chamber 40 having the inlets 42, 44 proximate the end 50. This is of particular advantage when the chamber 40 is flexible as herein above noted. The chamber wall 54 may be of a length designed in combination with the material of construction for enabling collapse thereof during selected aspiration and irrigation procedures mandated by the console 36. That is, a simulated lens capsule is provided.

Alternatively, as shown in FIG. 2, inlets 66, 72 may be provided on opposite ends 68, 74 of the chamber 62. This provides the advantage of utilizing the necked down portion 78 as a specific flexible portion for enabling collapse thereof as noted hereinabove and for more direct visualization of the fluidic circuit, also hereinabove noted.

Although there has been hereinabove described a specific test chamber for bimanual lens extraction in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. Test apparatus for bi-manual phaco needle apparatus, said test apparatus comprising:
    a chamber for establishing a fluidic circuit between an irrigation needle and an aspiration needle;
    a first inlet into said chamber for establishing fluid communication with an irrigation line, wherein said first inlet is sized for sealing around a handpiece portion supporting the irrigation needle; and
    a second inlet into said chamber for establishing fluid communication with an aspiration line, wherein said second inlet is sized for sealing around a handpiece portion supporting the aspiration needle;
    the chamber configured to enable visual monitoring of the fluidic circuit.

2. The test apparatus according to claim 1 wherein the first inlet and the second inlet are disposed proximate one end of said chamber.

3. The test apparatus according to claim 1 wherein the first inlet and the second inlet are disposed on opposite ends of said chamber.

4. The test apparatus according to claim 1 wherein said chamber is formed from a transparent material for enabling visual monitoring of the fluidic circuit.

5. The test apparatus according to claim 1, wherein the chamber is flexible.

6. A phacoemulsification apparatus, comprising:
    an irrigation handpiece having an irrigation needle;

an aspiration handpiece having an aspiration needle; and
a chamber configured to provide a fluidic circuit between the irrigation needle and the aspiration needle, the chamber comprising:
   a first inlet for sealably engaging a portion of at least one of the irrigation handpiece and the irrigation needle; and
   a second inlet for sealably engaging a portion of at least one of the aspiration handpiece and the aspiration needle;
   the chamber configured to enable visual monitoring of the fluidic circuit.

7. The test apparatus according to claim 6, wherein said chamber is formed from a transparent material for enabling visual monitoring of the fluidic circuit.

8. The test apparatus according to claim 6, wherein the chamber is flexible.

\* \* \* \* \*

UNITED STATES PATENT AND TRADEMARK OFFICE
CERTIFICATE OF CORRECTION

| | |
|---|---|
| PATENT NO. | : 7,373,850 B2 |
| APPLICATION NO. | : 10/290700 |
| DATED | : May 20, 2008 |
| INVENTOR(S) | : Kenneth Kadziauskas et al. |

It is certified that error appears in the above-identified patent and that said Letters Patent is hereby corrected as shown below:

Column 6, Claim No. 7: "The test apparatus according to claim 6, wherein said chamber is formed from a transparent material for enabling visual monitoring of the fluidic circuit" should be corrected to read: --The phacoemulsification apparatus according to claim 6, wherein said chamber is formed from a transparent material for enabling visual monitoring of the fluidic circuit.--

Column 6, Claim No. 8: "The test apparatus according to claim 6, wherein the chamber is flexible" should be corrected to read: --The phacoemulsification apparatus according to claim 6, wherein the chamber is flexible.--

Signed and Sealed this

Twenty-third Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,373,850 B2  Page 1 of 1
APPLICATION NO. : 10/290700
DATED : May 20, 2008
INVENTOR(S) : Kenneth Kadziauskas et al.

It is certified that error appears in the above-identified patent and that said Letters Patent is hereby corrected as shown below:

Column 6, Claim No. 7, lines 3-5: "The test apparatus according to claim 6, wherein said chamber is formed from a transparent material for enabling visual monitoring of the fluidic circuit" should be corrected to read: --The phacoemulsification apparatus according to claim 6, wherein said chamber is formed from a transparent material for enabling visual monitoring of the fluidic circuit.--

Column 6, Claim No. 8, lines 6-7: "The test apparatus according to claim 6, wherein the chamber is flexible" should be corrected to read: --The phacoemulsification apparatus according to claim 6, wherein the chamber is flexible.--

This certificate supersedes the Certificate of Correction issued September 23, 2008.

Signed and Sealed this

Fourteenth Day of October, 2008

JON W. DUDAS
*Director of the United States Patent and Trademark Office*